US008177714B2

(12) United States Patent
Lin

(10) Patent No.: US 8,177,714 B2
(45) Date of Patent: May 15, 2012

(54) SURGERY ASSISTING INSTRUMENT FOR RETINAL SURGERY

(76) Inventor: Po-Kang Lin, Taipei (TW)

( * ) Notice: Subject to any disclaimer, the term of this patent is extended or adjusted under 35 U.S.C. 154(b) by 565 days.

(21) Appl. No.: 11/959,463

(22) Filed: Dec. 19, 2007

(65) Prior Publication Data

US 2009/0163773 A1    Jun. 25, 2009

(51) Int. Cl.
*A61B 1/32* (2006.01)
(52) U.S. Cl. ........................................ 600/236; 600/235
(58) Field of Classification Search ................ 600/219, 600/235–246
See application file for complete search history.

(56) References Cited

U.S. PATENT DOCUMENTS 7,175,594 B2 *   2/2007   Foulkes ........................ 600/236
* cited by examiner

*Primary Examiner* — Eduardo C Robert
*Assistant Examiner* — Christina Negrelli
(74) *Attorney, Agent, or Firm* — Lin & Associates IP, Inc.

(57) ABSTRACT

A surgery assisting instrument for retinal surgery includes a cylinder and a strip connected with each other. The cylinder and the strip are made of a soft and biocompatible material. The cylinder is preferably connected with the strip at a side surface and close to an edge of the strip. The surgery assisting instrument is placed in a fornix around an eye at a position according to a retinal tear. The cylinder is pressed against the eye and the strip is pressed against the eyelid. Thus the retina is forced toward the back wall of the eye.

18 Claims, 3 Drawing Sheets

SURGERY ASSISTING INSTRUMENT FOR RETINAL SURGERY

BACKGROUND OF THE INVENTION

1. Field of the Invention

The present invention relates to an assisting instrument for eye surgery, and in particular to a surgery assisting instrument for eye surgery to repair a retinal detachment.

2. The Prior Arts

An ophthalmologist uses various instruments, such as opthalmoscope, slit lamp, and ultrasound, to examine retinas and check for eye diseases. Therefore, the doctor can detect eye problems at their earliest stage, when they're most treatable.

For retinal detachment, the treatment procedure is determined by the location and severity of the retinal detachment. If a retinal tear or a retinal hole is detected before detachment develops, the doctor may use laser surgery (photocoagulation) or freezing (cryopexy) to treat the tear or hole. The laser creates small burns and the freezing freezes small areas on the retina to create scar tissues around the retinal tear or hole. The scar tissues seal the tear and hold the retina to the back wall of the eye to prevent fluid from passing through the tear, leading to retinal detachment. If fluid has accumulated behind the retina and has lifted the retina off the back wall of the eye, the doctor may use one of pneumatic retinopexy, scleral buckling, and vitrectomy. Generally, these procedures push the retinal tear back against the back wall of the eye to close the tear and create scar tissues to seal the tear. With no new fluid passing through the retinal tear, fluid that had previously accumulated behind the retina is absorbed or drained. For a complicated retinal detachment, the doctor usually removes a small portion of the shrunk vitreous or scar tissue from the retinal surface with vitrectomy. If the detached retina has shrunk too much or the retina has wrinkled, the vitreous cavity is temporarily filled with expandable gas to push the retina back against the back wall of the eye. Eventually the eye absorbs the gas and replaces it with fluid that the eye normally produces.

The pneumatic retinopexy is a quick and effective surgery to treat the retinal detachment. First of all, the doctor freezes small areas of the retina to create scar tissues around the retinal tear. Then, a bubble of expandable gas is injected into the vitreous cavity, and the patient has to hold his or her head in a certain position for a few days after surgery to make sure the gas bubble seals the retinal tear. The pneumatic retinopexy is generally used when the retinal tear is located in the upper half of the retina. However, when retinal tear is located in the lower half of the retina, such as the 4-to-8 o'clock direction in FIG. 3, the retinal detachment can not be effectively treated with the pneumatic retinopexy.

SUMMARY OF THE INVENTION

A primary objective of the present invention is to provide a surgery assisting instrument for retinal surgery that is placed in an appropriate position around an eye according to the location of a retinal tear to push a retina back against the back wall of the eye. The surgery assisting instrument may even work in conjunction with photocoagulation, cryopexy, etc. to seal a retinal tear.

A surgery assisting instrument for retinal surgery according to the present invention includes a cylinder and a strip connected with each other. The cylinder and the strip are made of a soft biocompatible material with appropriate elasticity. The cylinder is preferably connected with the strip at a side surface and close to an edge of the strip. The surgery assisting device is placed at a formix outside of the eye. The strip is pressed against the eyelid and the cylinder is pressed against the eye, thereby forcing the retina against the back wall of the eye. Especially, the surgery assisting instrument is placed between an ocular conjunctiva and a palpebral conjunctiva. Due to the pressure of the eyelid and the tension of the sclera, the surgery assisting instrument is easily placed around the eye in the 4-to-8 o'clock direction or 2-to-10 o'clock direction according to the location of the retinal tear. Therefore, the retinal tear located in the lower half of the retina is pressed back against the wall of the eye. The retinal tear located in another position may also use the same method to treat.

The cylinder and the strip of the surgery assisting instrument according to the present invention is made of a material well tolerated by patients, such as silicone, plastic, or other appropriate biocompatible materials. The cylinder and the strip are extended to a certain length. The cross section of the cylinder can be a circle, a semicircle or a polygon according to the interior condition of the eye.

The cylinder and the strip according to the present invention are an integrally-formed single piece or two individual pieces connected by a fixing member. The cylinder is preferably connected with the strip at a side surface and close to an edge of the strip. Thus, when the strip is pressed against the palpebral conjunctiva, it is easier to adjust the cylinder to press the eye and to seal the retinal tear.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

Figure 1:
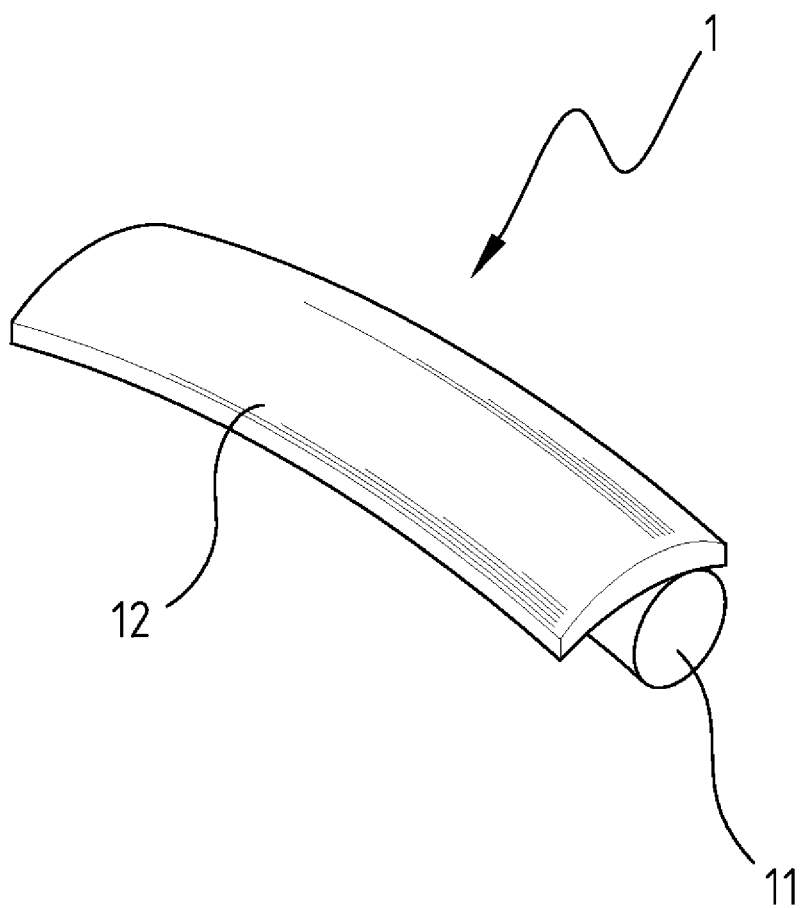
FIG. 1 is a perspective view showing a surgery assisting instrument for retinal surgery according to the present invention.
Figure 2:
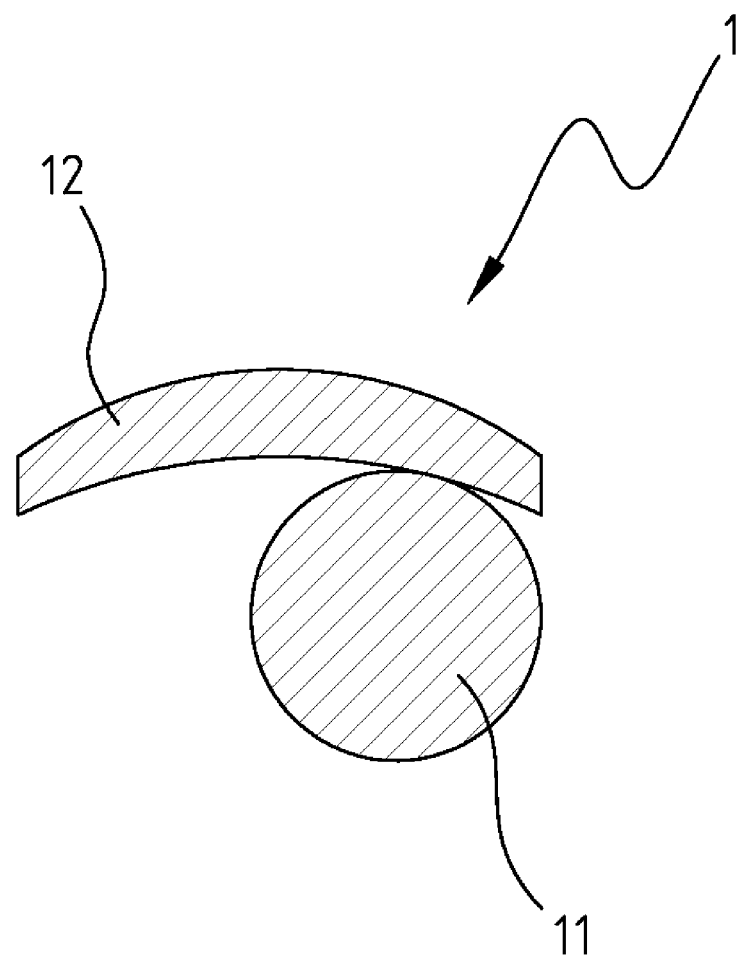
FIG. 2 is a cross sectional view showing the surgery assisting instrument for retinal surgery according to the present invention.

Referring to FIGS. 1 and 2, a surgery assisting instrument for retinal surgery 1 in accordance with the present invention is made of a soft and hypoallergenic material, such as silicone, plastic, or other appropriate materials. The surgery assisting instrument 1 includes a cylinder 11 and a strip 12, which are extended to a certain length according to the eye 2 and connected with each other. The cylinder 11 and the strip 12 may be an integrally-formed piece or two individual pieces connected by a fixing member, such as a suture. The cylinder 11 is preferably connected to the strip 12 at a side surface and close to an edge of the strip 12. The cross section of the cylinder 11 can be a circle, a semicircle or a polygon. The strip 12 is a thin and slightly curved piece.

Figure 3:
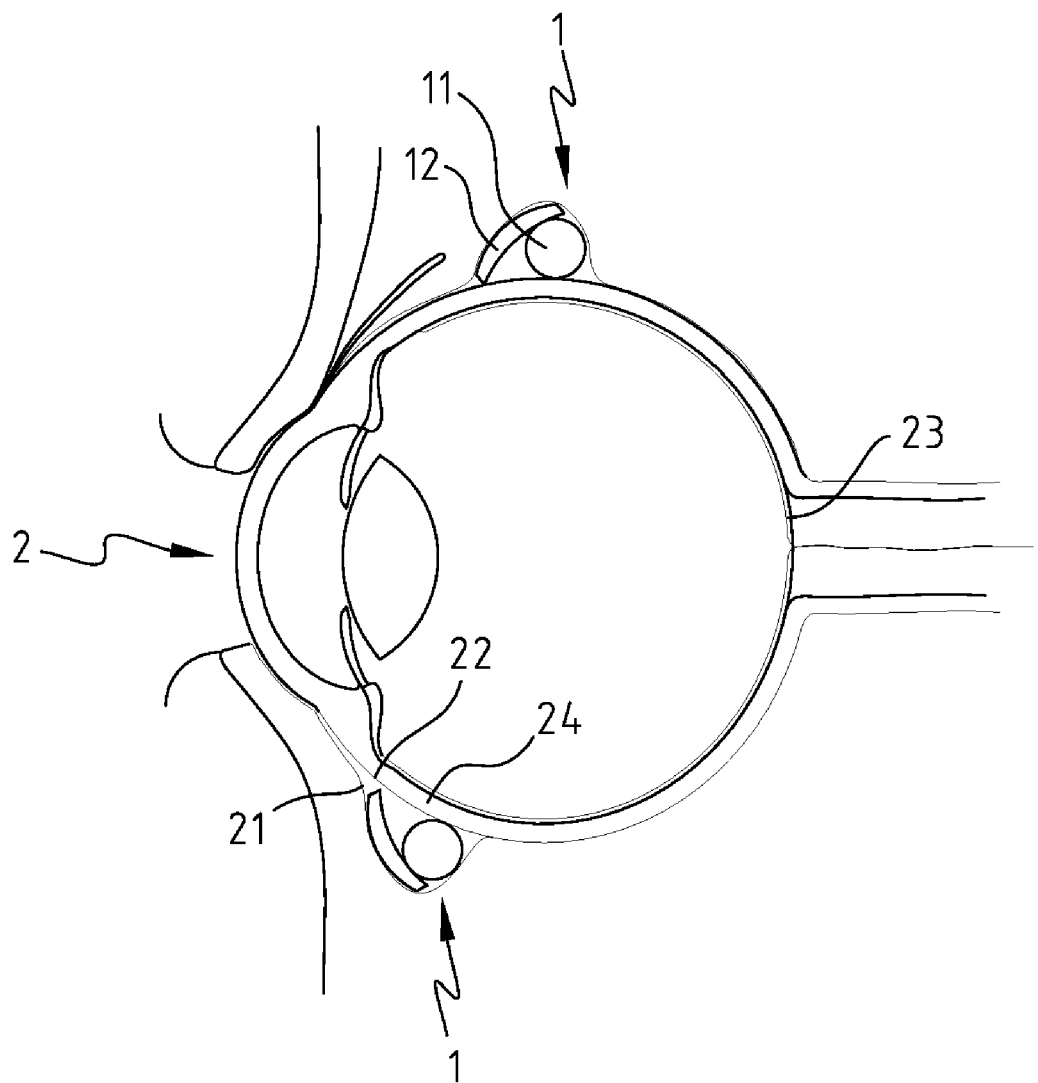
FIG. 3 is a schematic view showing the surgery assisting instrument for retinal surgery according to the present invention placed around the eye.

With reference to FIG. 3, the surgery assisting instrument for retinal surgery 1 according to the present invention is placed in a fornix between an ocular conjunctiva 22 and a palpebral conjunctiva 21. Due to the pressure of the eyelid and the tension of the sclera 24, the surgery assisting instrument 1 is easily placed around the eye 2 either in the 4-to-8 o'clock direction or 2-to-10 o'clock direction or in both directions according to the location of a retinal tear. The cylinder 11 is pressed against the eye 2 and the strip 12 is pressed against the eyelid so a force is applied on the eye 2 toward the retina 23. Therefore, the retina 23 is pressed back against the back wall of the eye 2. The surgery assisting instrument 1 can work in conjunction with an appropriate surgical procedure to treat the retina 23.

Although the present invention has been described with reference to the preferred embodiment thereof, it is apparent to those skilled in the art that a variety of modifications and changes may be made without departing from the scope of the present invention which is intended to be defined by the appended claims.

What is claimed is:

1. A surgery assisting instrument placed at a formix outside of an eye for retinal surgery, comprising
    a cylinder made of a soft material and extended along an axial direction thereof, the cylinder being pressed against the eye to push a retina against a back wall of the eye in the retinal surgery; and
    a strip made of a soft material and extended along the axial direction of the cylinder, the strip being wholly external to the cylinder and pressed against an eyelid of the eye in the retinal surgery;
    wherein an outer surface of the cylinder along the axial direction is connected with an outer side surface of the strip with the outer surface and the outer side surface both extending in the axial direction and in contact with each other along the axial direction.

2. The surgery assisting instrument as claimed in claim 1, wherein a cross section of the cylinder is one of a circle, a semicircle and a polygon.

3. The surgery assisting instrument as claimed in claim 1, wherein the cylinder is connected with the strip at a position close to an edge of the strip along the axial direction.

4. The surgery assisting instrument as claimed in claim 1, wherein the cylinder is connected with the strip by a fixing member.

5. The surgery assisting instrument as claimed in claim 4, wherein the fixing member is a suture.

6. The surgery assisting instrument as claimed in claim 1, wherein the cylinder and the strip are integrally formed.

7. The surgery assisting instrument as claimed in claim 1, wherein the cylinder and the strip are made of silicone.

8. The surgery assisting instrument as claimed in claim 2, wherein the cylinder and the strip are made of silicone.

9. The surgery assisting instrument as claimed in claim 3, wherein the cylinder and the strip are made of silicone.

10. The surgery assisting instrument as claimed in claim 4, wherein the cylinder and the strip are made of silicone.

11. The surgery assisting instrument as claimed in claim 5, wherein the cylinder and the strip are made of silicone.

12. The surgery assisting instrument as claimed in claim 6, wherein the cylinder and the strip are made of silicone.

13. The surgery assisting instrument as claimed in claim 1, wherein the cylinder and the strip are made of plastic.

14. The surgery assisting instrument as claimed in claim 2, wherein the cylinder and the strip are made of plastic.

15. The surgery assisting instrument as claimed in claim 3, wherein the cylinder and the strip are made of plastic.

16. The surgery assisting instrument as claimed in claim 4, wherein the cylinder and the strip are made of plastic.

17. The surgery assisting instrument as claimed in claim 5, wherein the cylinder and the strip are made of plastic.

18. The surgery assisting instrument as claimed in claim 6, wherein the cylinder and the strip are made of plastic.

\* \* \* \* \*